(12) United States Patent
Yamashita et al.

(10) Patent No.: US 12,035,924 B2
(45) Date of Patent: Jul. 16, 2024

(54) DISPLAY FOR CUTTING TOOL

(71) Applicant: J. MORITA MFG. CORP., Kyoto (JP)

(72) Inventors: Seiichiro Yamashita, Kyoto (JP);
Kyohei Kato, Kyoto (JP)

(*) Notice: Subject to any disclaimer, the term of this patent is extended or adjusted under 35 U.S.C. 154(b) by 205 days.

(21) Appl. No.: 17/148,562

(22) Filed: Jan. 14, 2021

(65) Prior Publication Data

US 2021/0219992 A1    Jul. 22, 2021

(30) Foreign Application Priority Data

Jan. 17, 2020  (JP) ................................ 2020-005840

(51) Int. Cl.
| | | |
|---|---|---|
| *A61B 17/16* | (2006.01) | |
| *A61C 1/00* | (2006.01) | |
| *A61C 5/42* | (2017.01) | |

(52) U.S. Cl.
CPC ........ *A61B 17/1626* (2013.01); *A61C 1/0015* (2013.01); *A61C 5/42* (2017.02)

(58) Field of Classification Search
CPC .............................. A61B 17/1626; A61C 5/42
See application file for complete search history.

(56) References Cited

U.S. PATENT DOCUMENTS

| | | |
|---|---|---|
| 2012/0122055 A1 | 5/2012 | Ramos et al. |
| 2013/0224678 A1 | 8/2013 | Yamashita et al. |
| 2015/0086937 A1 | 3/2015 | Katsuda et al. |
| 2017/0071713 A1* | 3/2017 | Nakai ................. A61B 6/5247 |
| 2017/0265961 A1 | 9/2017 | Kato et al. |
| 2019/0380813 A1 | 12/2019 | Kato et al. |

FOREIGN PATENT DOCUMENTS

| | | |
|---|---|---|
| CN | 102988028 | 3/2013 |
| CN | 106983572 | 7/2017 |
| CN | 108712111 | 10/2018 |
| CN | 110248619 | 9/2019 |
| | (Continued) | |

OTHER PUBLICATIONS

Extended Search Report in corresponding European Application No. 21151637.2, dated Jun. 10, 2021.
(Continued)

*Primary Examiner* — Cris L. Rodriguez
*Assistant Examiner* — Drew S Folgmann
(74) *Attorney, Agent, or Firm* — SOEI PATENT & LAW FIRM

(57) ABSTRACT

A root canal length measuring device includes a display for displaying a control mode figure indicating an execution control mode executed among a plurality of control modes and a control unit for controlling the display to display the figure. A plurality of elements for displaying the control mode figure include a shaft portion extending in an arc shape or a fan shape and a clockwise head portion and a counterclockwise head portion indicating a first direction and a second direction as rotation directions of a cutting tool, respectively. The control unit controls the display according to the execution control mode in a root canal treatment device so that, among the plurality of elements, an entirety or a part of the shaft portion and the clockwise head portion and/or the counterclockwise head portion are displayed on the display.

20 Claims, 10 Drawing Sheets

(56) References Cited

FOREIGN PATENT DOCUMENTS

| | | |
|---|---|---|
| JP | H9-248311 | 9/1997 |
| JP | 2011-135950 | 7/2011 |
| JP | 2013-172839 | 9/2013 |
| JP | 2015-083116 | 4/2015 |
| JP | 2017-170133 | 9/2017 |
| JP | 2018-143631 | 9/2018 |
| JP | 2018-149169 | 9/2018 |
| JP | 2019-195719 | 11/2019 |

OTHER PUBLICATIONS

Notice of Decision to Grant a Patent issued in Japanese Patent Application No. P2020-005840, dated Nov. 29, 2022 (with English partial translation).
Notice of Intention to Grant issued in European Patent Application No. 21151637.2 dated Mar. 16, 2023.

* cited by examiner

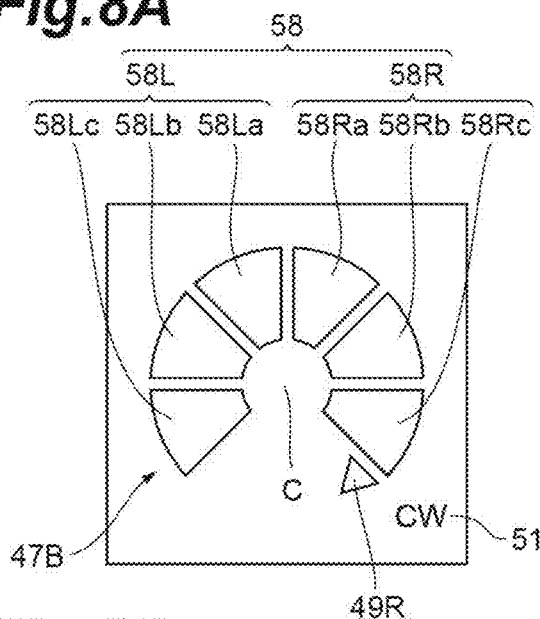
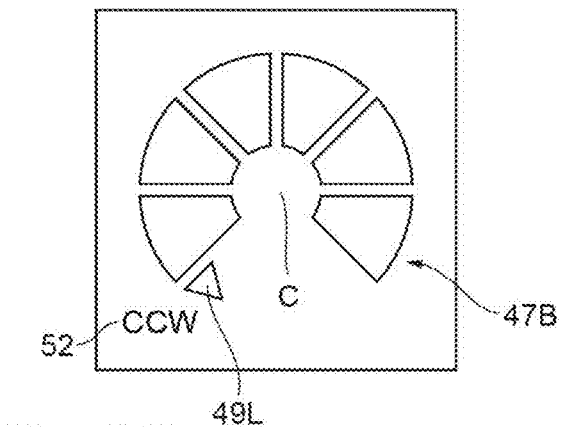
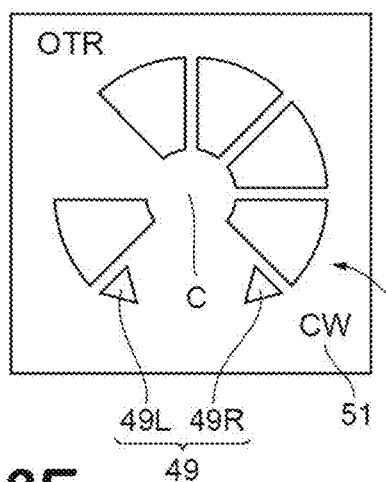
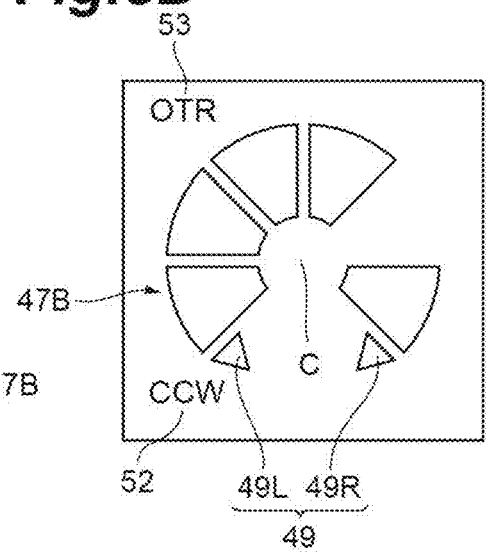
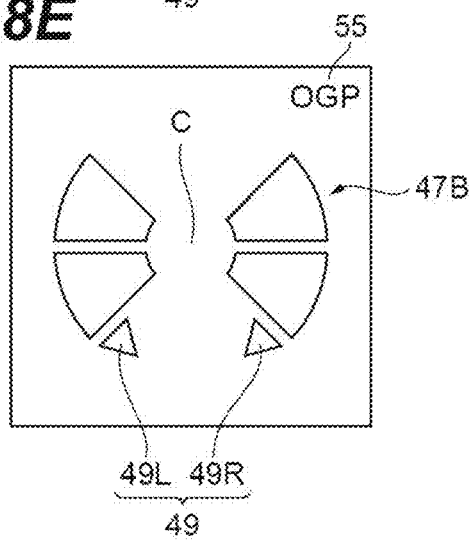

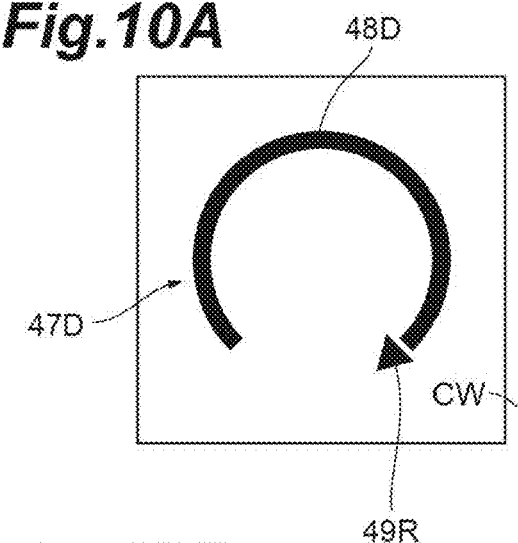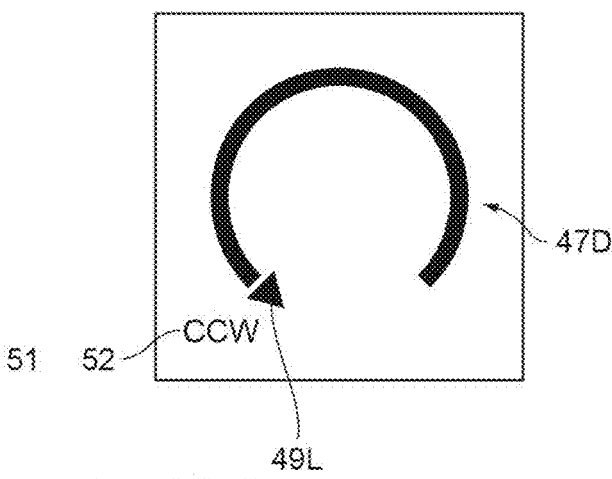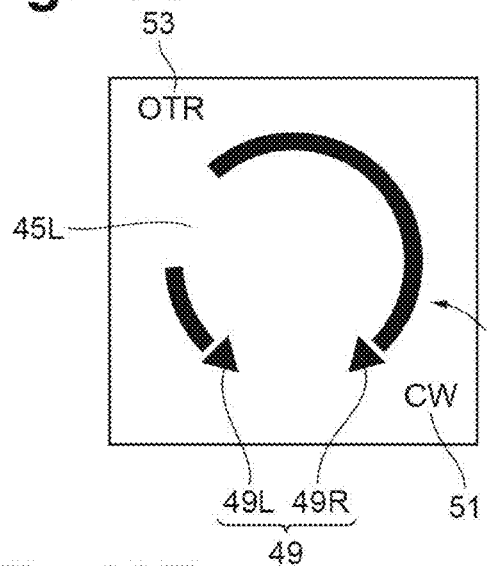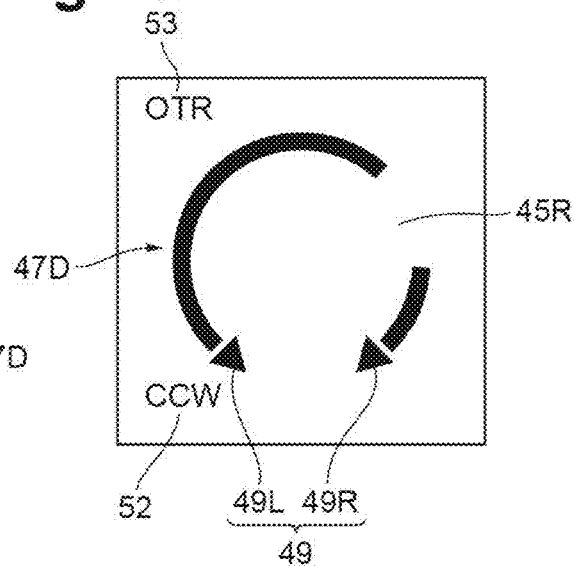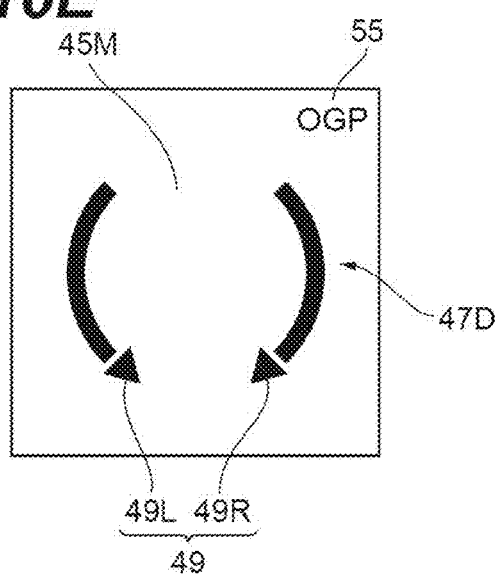

DISPLAY FOR CUTTING TOOL

CROSS-REFERENCE TO RELATED APPLICATIONS

This application claims the benefit of priority from Japanese Patent Application No. 2020-005840, filed on Jan. 17, 2020, the entire contents of which are incorporated herein by reference.

BACKGROUND

A root canal treatment apparatus cuts the root canal wall of the patient's tooth by rotating a cutting tool attached to a handpiece (root canal treatment device) to enlarge the root canal. In the apparatuses described in Japanese Unexamined Patent Publication No. 2018-149169, Japanese Unexamined Patent Publication No. 2015-83116, and Japanese Unexamined Patent Publication No. 2017-170133, a cutting tool such as a file or a reamer is attached to a head portion of a handpiece, and the cutting tool rotates clockwise or counterclockwise.

Each of the apparatuses includes a display unit provided in a control box or the like. The display unit displays the position or the rotation direction of the distal end of the cutting tool in the root canal. In the apparatus described in Japanese Unexamined Patent Publication No. 2018-149169, the display unit includes a rotation display unit that displays the direction of rotation of the cutting tool and the like.

SUMMARY

As also described in Japanese Unexamined Patent Publication No. 2015-83116 and Japanese Unexamined Patent Publication No. 2017-170133, in order to improve cutting efficiency or perform appropriate cutting, the cutting tool of the root canal treatment device performs cutting in a plurality of driving patterns (in other words, a rotation mode or a control mode). Accordingly, more desirable root canal enlargement is performed by cutting tool driving in which clockwise and counterclockwise are appropriately combined. The conventional rotation display unit described above can display the rotation direction of the cutting tool, but it is difficult for the user to check various control modes of the cutting tool on the rotation display unit.

The disclosure will describe a display apparatus and a display control method that allow a user to grasp the control mode of a root canal treatment device at a glance.

An example display apparatus for displaying a control mode of a cutting tool attached to a root canal treatment device includes: a display unit that displays a figure indicating an execution control mode executed among a plurality of control modes; and a control unit that controls the display unit to display the figure. A plurality of elements for displaying the figure may include a shaft portion extending in an arc shape or a band portion extending in a fan shape and a first head portion and a second head portion that are disposed at a first end and a second end of the shaft portion or the band portion to indicate a first direction and a second direction as rotation directions of the cutting tool, respectively. The control unit may control the display unit according to the execution control mode in the root canal treatment device so that, among the plurality of elements, an entirety or a part of the shaft portion or the band portion and the first head portion and/or the second head portion are displayed on the display unit.

Another example display control method in a display apparatus that displays a control mode of a cutting tool attached to a root canal treatment device includes a display unit that displays a figure indicating an execution control mode executed among a plurality of control modes. The display control method may include: controlling the display unit according to the execution control mode in the root canal treatment device so that, among a plurality of elements for displaying the figure, an entirety or a part of a shaft portion extending in an arc shape or a band portion extending in a fan shape and a first head portion and/or a second head portion that are disposed at a first end and a second end of the shaft portion or the band portion to indicate a first direction and a second direction as rotation directions of the cutting tool, respectively, are displayed on the display unit. The plurality of elements include the shaft portion or the band portion and the first head portion and the second head portion.

In the display apparatus and the display control method, the execution control mode actually executed may be shown as a figure on the display unit. In order to display this figure, a plurality of elements may be provided in the display unit. By the control unit (or the display control method), the entirety or a part of the shaft portion or the band portion extending in an arc shape or a fan shape and the first head portion and/or the second head portion disposed at the first end and the second end of the shaft portion or the band portion may be displayed on the display unit. As a display form (display method) of the shaft portion or the band portion and the head portion, instead of simply turning on and off the shaft portion or the band portion and the head portion, various forms can be adopted in which a part of the shaft portion or the band portion is displayed or either or both of the head portions are displayed. Therefore, it is possible to display a figure that matches the rotation mode of the cutting tool, or the control mode, and it becomes easy for the user to grasp at a glance the execution control mode executed in the root canal treatment device. The term "displaying a figure" may include a mode in which the shaft portion or the band portion and a predetermined portion of the head portion continue to light and a mode in which the shaft portion or the band portion and a predetermined portion of the head portion blink.

The control unit may cause the display unit to display at least a part of the shaft portion or the band portion and both the first head portion and the second head portion in the case of the predetermined execution control mode. In this case, only a part of the shaft portion or the band portion may be displayed, and together with this, both the first head portion and the second head portion may be displayed. Therefore, it is possible to express not only a simple rotation in the first or second direction but also a complicated movement of the cutting tool.

The plurality of control modes may include a first mode in which a rotation direction is only the first direction, a second mode in which a rotation direction is only the second direction, a third mode in which a main rotation direction of the rotation directions is the first direction and a secondary rotation direction of the rotation directions is the second direction, and a fourth mode in which the main rotation direction of the rotation directions is the second direction and the secondary rotation direction of the rotation directions is the first direction, and the predetermined execution control mode may not include the first mode and the second mode and may include at least one of the third mode and the fourth mode. In the third mode and the fourth mode, unlike in the first mode and the second mode, the cutting tool may make complicated movements. In either the third mode or the fourth mode, a part of the shaft portion or the band portion and both the first head portion and the second head portion may be displayed, so that the complicated movement of the cutting tool can be expressed.

The plurality of control modes may include at least two or more of a first mode in which a rotation direction is only the first direction, a second mode in which a rotation direction is only the second direction, a third mode in which a main rotation direction of the rotation directions is the first direction and a secondary rotation direction of the rotation directions is the second direction, and a fourth mode in which the main rotation direction of the rotation directions is the second direction and the secondary rotation direction of the rotation directions is the first direction. By appropriately combining the display of the shaft portion or the band portion and the display of the head portion, it is possible to express information indicating whether the rotation direction is the first direction or the second direction, information indicating whether the main rotation direction is the first direction or the second direction, and the like. The user can easily grasp which control mode among the plurality of control modes is being executed.

When the execution control mode is the first mode, the control unit may cause the display unit to display an entirety or a part of the shaft portion or the band portion and only the first head portion, and when the execution control mode is the second mode, the control unit may cause the display unit to display an entirety or a part of the shaft portion or the band portion and only the second head portion. In this case, the user can easily grasp whether the cutting tool is rotating in the first direction or in the second direction by switching the head portion to be displayed under the control of the control unit.

When the execution control mode is the third mode, the control unit may cause the display unit to display both the first head portion and the second head portion and may cause the display unit not to display only a portion close to the second end of the shaft portion or the band portion, and when the execution control mode is the fourth mode, the control unit may cause the display unit to display both the first head portion and the second head portion and may cause the display unit not to display only a portion close to the first end of the shaft portion or the band portion. In this case, the user can easily grasp that the cutting tool is rotating in both the first direction and the second direction. Since one of the first end side and the second end side of the shaft portion or the band portion may be longer than the other, the user can easily grasp which is the main rotation direction.

The plurality of control modes may include a fifth mode in which the rotation direction repeats the first direction and the second direction. By appropriately combining the display of the shaft portion or the band portion and the display of the head portion, it is possible to express that the rotation in the first direction and the rotation in the second direction are repeated. The user can easily grasp which control mode among the plurality of control modes is being executed.

When the execution control mode is the fifth mode, the control unit may cause the display unit to display both the first head portion and the second head portion and may cause the display unit not to display only a middle portion between the first end and the second end of the shaft portion or the band portion. In this case, since the lengths of the left and right portions (first end side and second end side) of the shaft portion or the band portion may be equal, the user can easily grasp that the cutting tool is repeatedly rotating in the first direction and the second direction.

The shaft portion or the band portion may include at least four or more segments arranged in an arc shape or a fan shape. In this case, by turning on, turning off, or blinking each segment of the shaft portion or the band portion, the user can more easily grasp the control mode. Since the display control of a figure is also simplified, it is easy to control the display of a figure.

BRIEF DESCRIPTION OF THE DRAWINGS

FIGS. 8A to 8E are diagrams showing display modes of first to fifth modes in a second modification example.

FIGS. 10A to 10E are diagrams showing display modes of first to fifth modes in a fourth modification example.

DETAILED DESCRIPTION

Figure 1:
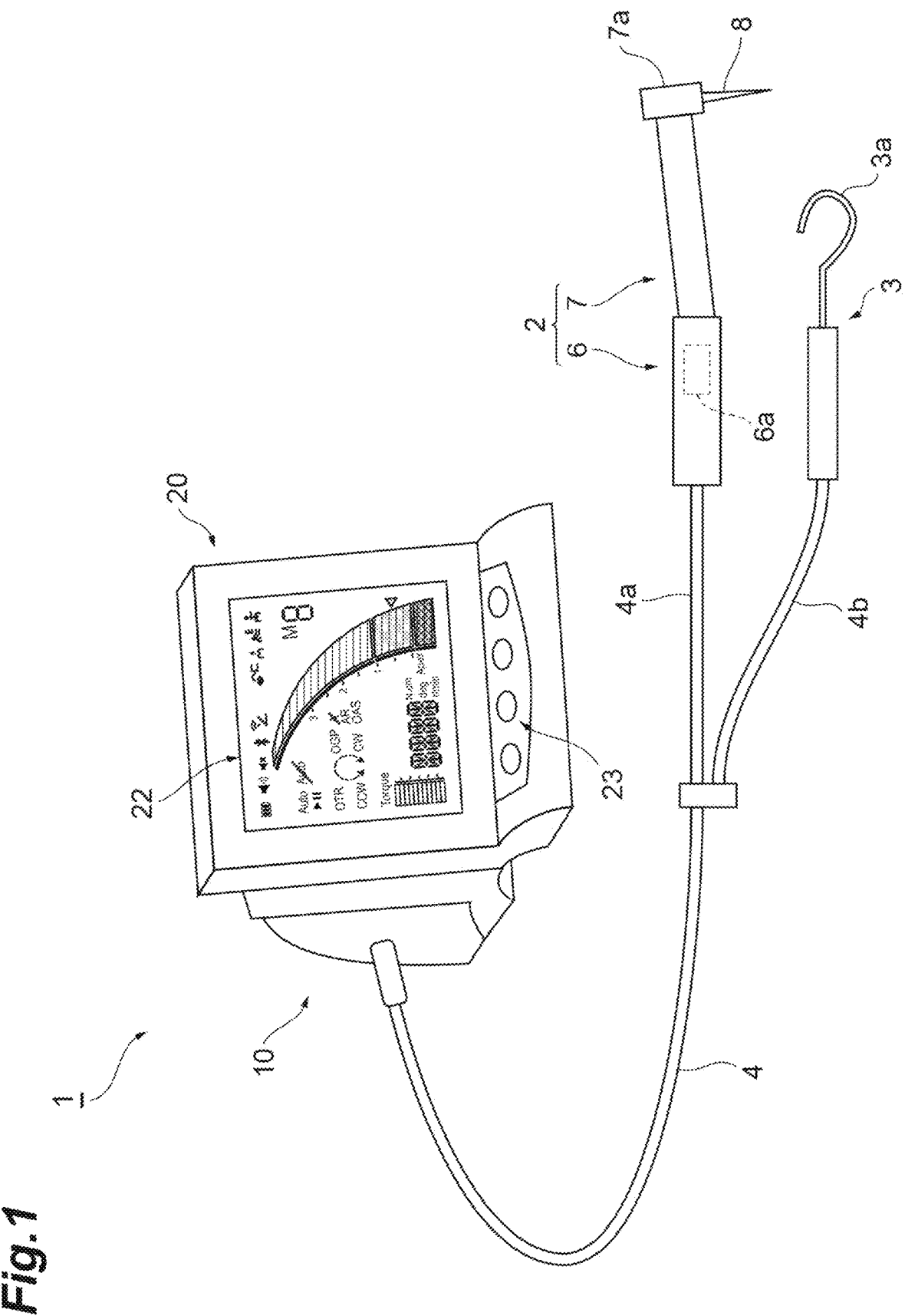
FIG. 1 is a diagram showing a root canal treatment apparatus to which an example display apparatus is applied.

In the following description, with reference to the drawings, the same reference numbers are assigned to the same components or to similar components having the same function, and overlapping description is omitted.

First, an example root canal treatment apparatus 1 to which an example display apparatus is applied will be described with reference to FIGS. 1 and 2. The root canal treatment apparatus 1 is a dental treatment apparatus for enlarging the root canal by cutting the root canal wall of the patient's tooth. The root canal treatment apparatus 1 includes a root canal treatment device 10 having an instrument 2 that is a treatment tool for enlarging the root canal, a root canal length measuring device (display apparatus) 20 for setting the driving mode of the instrument 2 in the root canal treatment device 10 or displaying the driving state of the instrument 2 and the treatment state of the tooth, and a tablet 30 that is used at a position away from the root canal length measuring device 20 and displays the same items and contents as the display screen of the root canal length measuring device 20.

Figure 2:
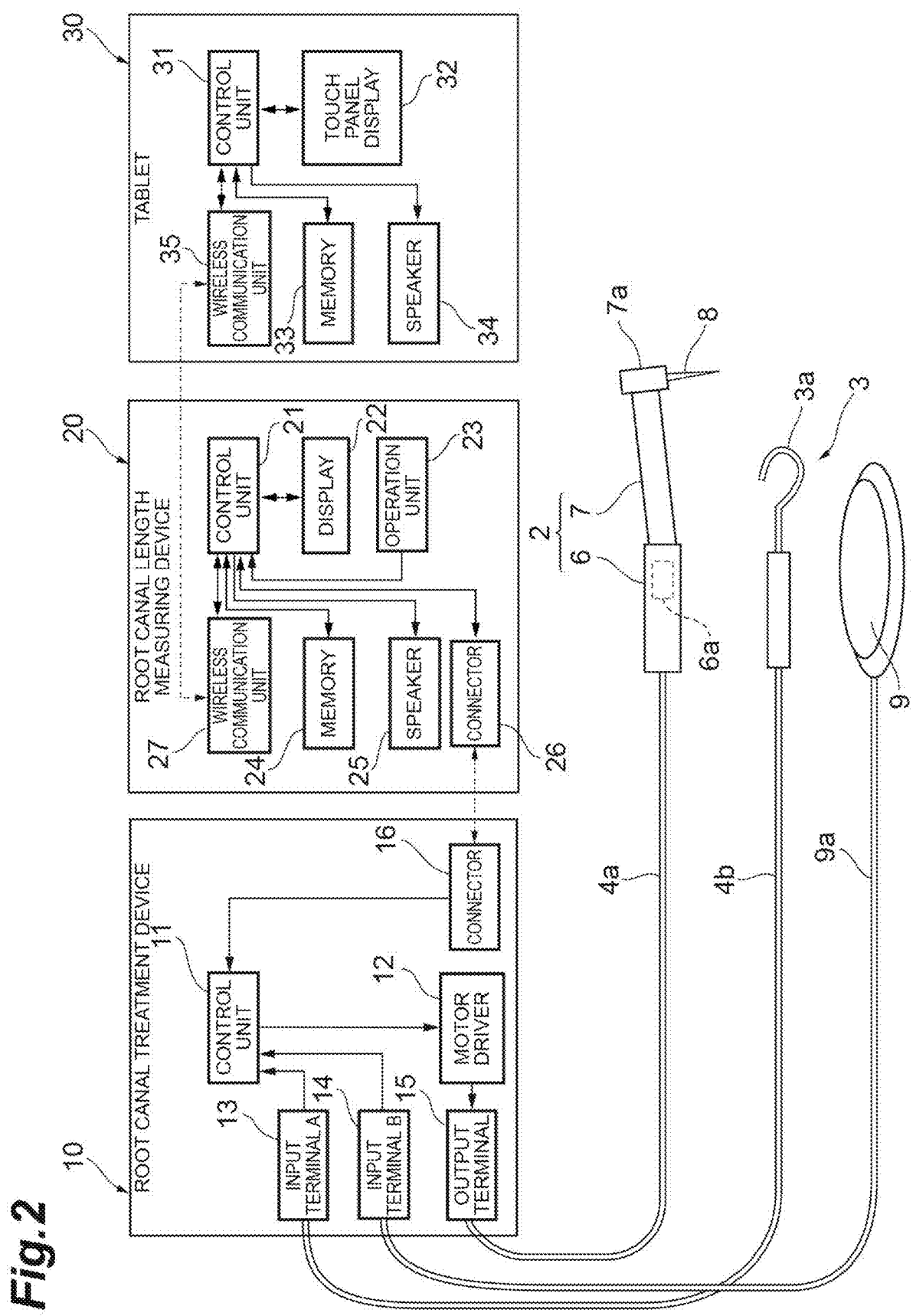
FIG. 2 is a diagram showing the schematic configuration of a root canal treatment system including a root canal treatment apparatus and a tablet.

The main body of the root canal treatment device 10 is attached to the back surface of the root canal length measuring device 20, for example, as shown in FIG. 1. The root canal treatment device 10 is attached to the root canal length measuring device 20 when a dentist who is a user of the apparatus performs root canal treatment. The root canal length measuring device 20 may be connected to the root canal treatment device 10, and an input from the user regarding the driving control of the instrument 2 is received through an operation unit 23 and a control signal is transmitted to a control unit 11 of the root canal treatment device 10. In addition, the root canal length measuring device 20 may receive various signals output from the root canal treatment device 10 and displays necessary information on a display (display unit) 22. The root canal length measuring device 20 can also be applied to treatments other than the root canal enlargement. When a treatment other than the root canal enlargement is performed, another treatment device different from the root canal treatment device 10 is attached to the back surface of the root canal length measuring device 20.

The root canal treatment device 10 includes the control unit 11, a motor driver 12, an input terminal A 13, an input terminal B 14, an output terminal 15, and a connector 16, and these are housed in a main body (housing) attached to the root canal length measuring device 20. In addition, the root canal treatment device 10 includes an oral electrode 3, which is connected to the control unit 11 through the input terminal A 13 and an oral electrode cable 4b, and the instrument 2, which is connected to the motor driver 12 through the output terminal 15 and an instrument cable 4a. As shown in FIG. 1, the instrument cable 4a and the oral electrode cable 4b may be provided so as to branch from the middle of one cable 4 connected to the main body. In the cable 4 (the instrument cable 4a and the oral electrode cable 4b), a power supply lead wire for driving the instrument 2, a signal lead wire for transmitting various signals, and the like are provided.

The root canal treatment device 10 includes a foot controller 9 connected to the control unit 11 through the input terminal B 14 and a cable 9a. In addition, although not shown, the root canal treatment device 10 includes a battery for supplying necessary power to the root canal treatment apparatus 1. In addition, a power cable for supply of power may be attached to either the root canal treatment device 10 or the root canal length measuring device 20.

The instrument 2 includes a handpiece 7 held by the user to enlarge the root canal and a motor unit 6 detachably connected to the proximal end side of the handpiece 7. The handpiece 7 includes a head portion 7a provided at its distal end, and a cutting tool (a file, a reamer, or the like) 8 is held in the head portion 7a. The motor unit 6 has a built-in micromotor 6a for rotationally driving the cutting tool 8 through a rotational force transmission mechanism in the handpiece 7. The cutting tool 8 functions as a first electrode of a root canal length measuring circuit for detecting the root canal length, or the position of the distal end of the cutting tool 8 in the root canal. The oral electrode 3 includes a hook portion 3a provided at its distal end. When root canal enlargement is performed, the hook portion 3a is hooked on the corner of the patient' mouth and functions as a second electrode of the root canal length measuring circuit. The foot controller 9 is an operation unit for the user to step thereon to control the driving of the cutting tool 8 by the micromotor 6a.

The control unit 11 is a computer including a processor, such as a CPU, and a storage device including a RAM, a ROM, and the like. The control unit 11 receives an operation signal from the foot controller 9 and also receives an operation signal from the root canal length measuring device 20 to control the driving of the motor driver 12.

The root canal length measuring device 20 may include a control unit 21, the display 22, the operation unit 23, a memory 24, a speaker 25, a connector 26, and a wireless communication unit 27, which are provided in a main body (housing). With the root canal treatment device 10 attached to the root canal length measuring device 20, various signals can be transmitted and received between the root canal length measuring device 20 and the root canal treatment device 10 through the connector 26 and the connector 16. The control unit 21 is a computer including a processor, such as a CPU, and a storage device including a RAM, a ROM, and the like. The control unit 21 issues a command to the control unit 11 of the root canal treatment device 10 based on the control mode, the user setting mode, and the like of the cutting tool 8 input through the operation unit 23. In addition, the control unit 21 controls the display of the display 22 based on signals transmitted from the control unit 11 indicating the driving state of the instrument 2 and the treatment state of the tooth. In addition, the control unit 21 transmits a signal to the tablet 30 through the wireless communication unit 27 so that the same display items and contents as those displayed on the display 22 are displayed on the tablet 30. So-called mirroring control is performed between the root canal length measuring device 20 and the tablet 30. The "treatment state of the tooth" may be a concept including the root canal length described above.

The operation unit 23 is an input device for the user to perform the control mode of the cutting tool 8 that needs to be executed in the treatment or various settings suitable for itself (for example, the number of rotations of the cutting tool 8 or the desired root canal length) or to turn on and off the power. The speaker 25 emits, for example, an operation sound during setting or a sound corresponding to the root canal length during treatment (including a warning sound when the distal end of the cutting tool 8 reaches the desired root canal length).

A program for controlling the display of the display 22, which will be described in detail below, is stored in the memory 24. In addition, a program for performing various controls of the root canal treatment apparatus 1 may be stored in the memory 24. In addition, setting information, such as the number of rotations, is stored in the memory 24.

The root canal treatment device 10 and the root canal length measuring device 20 may measure the root canal length during treatment for the patient. A closed circuit is formed by the cutting tool 8 inserted into the root canal of the tooth and the oral electrode 3 hung on the corner of the patient's mouth. By measuring the impedance between the cutting tool 8 and the oral electrode 3, the distance from the distal end position (root apex) of the tooth to the distal end of the cutting tool 8 is measured. The measured distance is assumed to be the root canal length. The root canal length measuring circuit may be formed in the root canal length measuring device 20, or may be formed in the root canal treatment device 10. Alternatively, the root canal length measuring circuit may be formed by both the root canal length measuring device 20 and the root canal treatment device 10.

The tablet 30 may be a terminal used by a user or a person (such as another dentist or a dental assistant) other than the user. The tablet 30 may include a control unit 31, a touch panel display 32, a memory 33, a speaker 34, and a wireless communication unit 35. Since the wireless communication unit 35 is provided, the tablet 30 can wirelessly communicate with the wireless communication unit 27 of the root canal length measuring device 20. The control unit 31 is a computer including a processor, such as a CPU, and a storage device including a RAM, a ROM, and the like. The control unit 31 receives a signal transmitted from the root canal length measuring device 20 and performs mirroring control to control the display of the touch panel display 32. The touch panel display 32 of the tablet 30 may have the same function as the operation unit 23 of the root canal length measuring device 20. Instead of the memory 33, the ROM of the control unit 31 may be used.

Subsequently, the display control in the root canal length measuring device 20 will be described with reference to FIGS. 3A and 3B. The root canal length measuring device 20 may be a display apparatus that displays various states in the root canal treatment apparatus 1, for example, the driving state of the instrument 2 and the treatment state of the tooth. By visually checking the display 22 while treating the patient, the user can check whether or not the situation of treatment is appropriate or check whether or not the desired treatment state is realized. In the example, the root canal length measuring device 20 may display the control mode of the cutting tool 8 attached to the handpiece 7 that is a part of the root canal treatment device 10. The display 22 may display a figure showing an execution control mode that is actually executed during the treatment among a plurality of control modes that can be executed in the root canal treatment apparatus 1.

First, a plurality of control modes that can be executed in the root canal treatment device 10 will be described. The plurality of control modes are defined based on the rotation direction and the rotation mode (various modes including whether the cutting tool 8 continues to rotate in the same direction, rotates in the opposite direction, or temporarily stops) of the cutting tool 8. These control modes are stored in the memory 24 of the root canal length measuring device 20. The plurality of control modes may include at least a first mode (hereinafter, referred to as a CW mode) in which the rotation direction of the cutting tool 8 is only clockwise (first direction) and a second mode (hereinafter, referred to as a CCW mode) in which the rotation direction of the cutting tool 8 is only counterclockwise (second direction). The two types of control modes are modes in which the cutting tool 8 continuously rotates in the same direction until the user steps on the foot controller 9 to stop the rotation.

Figure 5A:
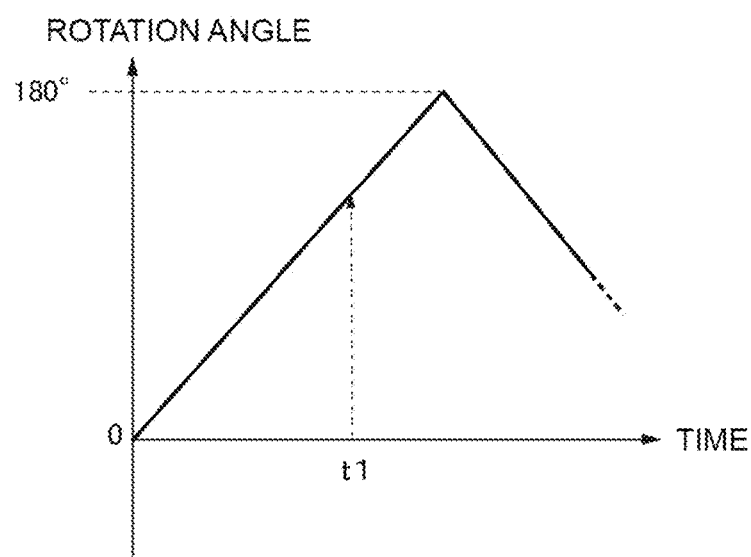
FIG. 5A is a diagram showing the rotation of a cutting tool in a third mode.
Figure 5B:
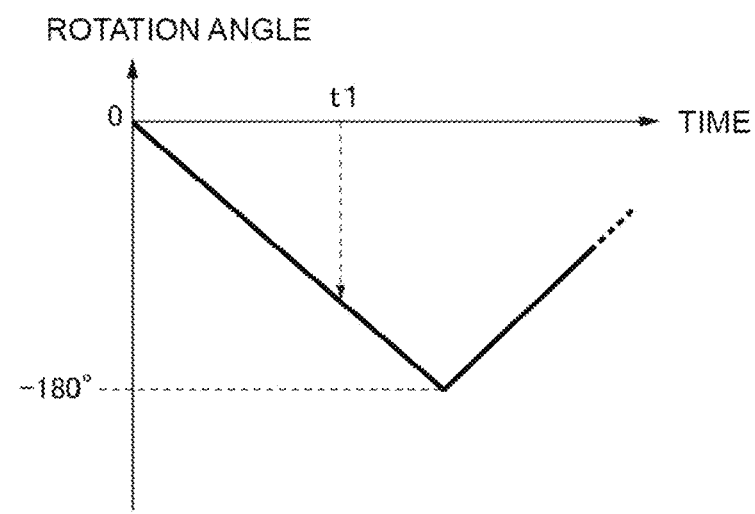
FIG. 5B is a diagram showing the rotation of the cutting tool in a fourth mode.
Figure 5C:
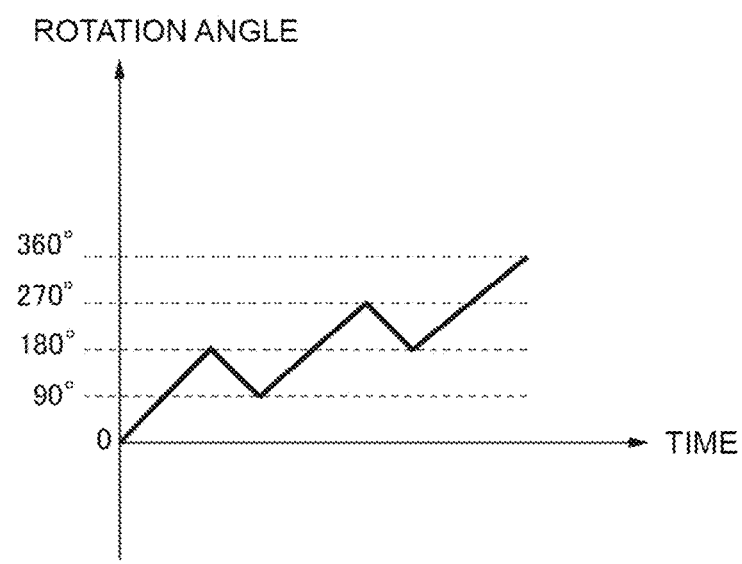
FIG. 5C is a diagram showing the rotation of the cutting tool in a fifth mode.

Next, other control modes will be described with reference to FIGS. 5A to 5C. As shown in FIG. 5A, the plurality of control modes include a third mode (hereinafter, referred to as an OTR-CW mode) in which the rotation direction in the half or more of the driving period of the cutting tool 8 is clockwise and the rotation direction in the other part of the driving period of the cutting tool 8 is counterclockwise. The control unit 21 can detect the rotation angle. In the OTR-CW mode, while the cutting tool 8 is rotating clockwise, when the rotation angle becomes 180° after time t1 at which the load in the rotation direction applied to the cutting tool 8 when cutting the tooth, or the value of torque (hereinafter, referred to as a torque value), becomes equal to or greater than a predetermined threshold value, the cutting tool 8 rotates counterclockwise (reversed). In the OTR-CW mode, the main rotation direction of the cutting tool 8 is clockwise, and in a predetermined case (the secondary rotation direction), the rotation direction of the cutting tool 8 is counterclockwise. In addition, as shown in FIG. 5B, the plurality of control modes include a fourth mode (hereinafter, referred to as an OTR-CCW mode) in which the rotation direction in the half or more of the driving period of the cutting tool 8 is counterclockwise and the rotation direction in the other part of the driving period of the cutting tool 8 is clockwise. In the OTR-CCW mode, while the cutting tool 8 is rotating counterclockwise, when the rotation angle becomes −180° after time t1 at which the load in the rotation direction applied to the cutting tool 8 when cutting the tooth, or the torque value, becomes equal to or greater than a predetermined threshold value, the cutting tool 8 rotates clockwise (reversed). In the OTR-CCW mode, the main rotation direction of the cutting tool 8 is counterclockwise, and in a predetermined case (the secondary rotation direction), the rotation direction of the cutting tool 8 is clockwise. The "main rotation direction" means that the period during which the cutting tool 8 rotates in the rotation direction is longer than the period during which the cutting tool 8 rotates in the other rotation direction, and usually means that the root canal wall is cut in the rotation direction. In FIGS. 5A to 5C, the vertical axis indicates a cumulative value of the rotation angle, and clockwise is positive and counterclockwise is negative. The control unit 11 can calculate the torque value based on, for example, a value of current flowing through the load detection resistor provided in the motor driver 12.

Both the OTR-CW mode and the OTR-CCW mode are control modes in which it is possible to improve tooth cutting efficiency while preventing the cutting tool from being damaged by the load applied to the cutting tool 8. These control modes are disclosed in, for example, Japanese Unexamined Patent Publication No. 2015-83116. In order to perform such control, the root canal length measuring device 20 can detect a torque value based on a signal transmitted from the root canal treatment device 10, and a predetermined threshold value is stored in the memory 24. The predetermined threshold value is a value that can be arbitrarily set by the user using the root canal length measuring device 20 or the tablet 30. The above 180°, which is a turning point, can also be changed and set. In addition, "OTR" is an abbreviation for Optimum Torque Reverse, "CW" is an abbreviation for clockwise, and "CCW" is an abbreviation for counterclockwise.

As shown in FIG. 5C, the plurality of control modes include a fifth mode (hereinafter, referred to as an OGP mode) in which the rotation direction of the cutting tool 8 repeats clockwise and counterclockwise. In the OGP mode, for example, when the rotation angle of the cutting tool 8 that rotates clockwise reaches 180°, the cutting tool 8 rotates counterclockwise. Then, when the rotation angle of the cutting tool 8 reaches 90°, the cutting tool 8 rotates clockwise. Thereafter, each time the rotation angle reaches 180+90°×N (N is a natural number), control is performed such that the cutting tool 8 is returned by 90° counterclockwise. The OGP mode is a control mode in which the root canal can be appropriately cut regardless of the shape of the root canal, for example. This control mode is disclosed in, for example, Japanese Unexamined Patent Publication No. 2017-170133. The above 180° or 90° can be changed and set. In this case, the angle of rotation (return) counterclockwise is smaller than the angle of rotation clockwise. Accordingly, the cutting tool 8 rotates in the second direction only at a part of the angle at which the cutting tool 8 rotates in the first direction. In the OGP mode, the cutting tool 8 may rotate (or return) clockwise with the counterclockwise rotation as a basis. Accordingly, the form shown in FIG. 5C may be a control mode in which the first direction and the second direction are reversed. In addition, "OGP" is an abbreviation for Optimum Grid Path.

In the root canal treatment apparatus 1, one of the control modes can be selected by the user operating the operation unit 23 located below the display 22. The operation unit 23 includes one or more buttons (button switches), and the user selects one of the control modes while viewing the control mode selection notation shown on the display 22, for example. Each of the control unit 11 and the control unit 21 performs a predetermined process according to the selected control mode (execution control mode). The control unit 11 receives an operation signal from the root canal length measuring device 20 and performs driving control according to the control mode selected for the motor driver 12. The motor driver 12 drives the micromotor 6a so that the micromotor 6a performs a rotational operation according to each control mode. For the display 22 and the speaker 25, the control unit 21 controls screen display or sound output according to the selected control mode. In addition, by the user operating the touch panel display 32 of the tablet 30, any control mode can be selected in the same manner as described above.

Referring back to FIG. 3A, the control unit 21 may control the display 22 so that a figure indicating the execution control mode is displayed on the display 22. As shown in FIG. 3A, an operation mode display portion 41 for displaying a setting mode selected by the user, a dot display portion 42 including a large number of elements for displaying the measured root canal length in detail, a zone display portion 43 for displaying the root canal length in a stepwise manner by dividing the root canal length into a plurality of zones, a numerical display portion 44 for displaying the number of rotations of the cutting tool 8 and the like, and a dot display portion 46 including a large number of elements for displaying the value of torque applied to the cutting tool 8 are provided on the display 22.

In addition, a control mode FIG. 47 and a control mode character notation 50 for indicating the execution control mode being executed among the various control modes described above are provided on the display 22. The control mode character notation 50 includes character strings corresponding to the various modes described above: CW notation 51, CCW notation 52, OTR notation 53, and OGP notation 55, which are disposed at the four corners of the control mode FIG. 47. These character notations are displayed alone or in combination.

Figure 4:
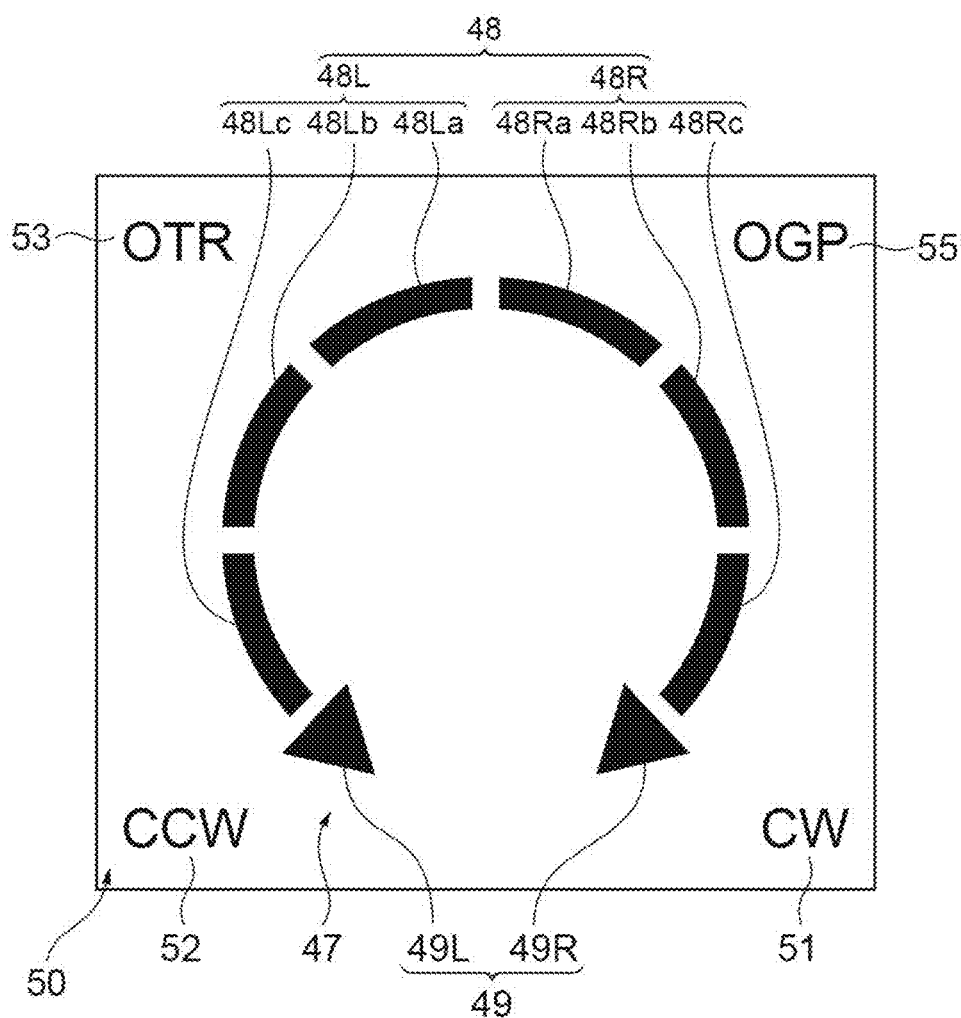
FIG. 4 is a diagram showing a control mode figure and a control mode character notation in FIG. 3A.

As shown in FIG. 4, a plurality of elements for displaying the control mode FIG. 47 are a shaft portion 48 extending in an arc shape and a clockwise head portion (first head portion) 49R and a counterclockwise head portion (second head portion) 49L disposed at the lower right end (first end) and the lower left end (second end) of the shaft portion 48, respectively. A direction display portion 49 is formed by the clockwise head portion 49R and the counterclockwise head portion 49L, and the clockwise head portion 49R and the counterclockwise head portion 49L indicate clockwise and counterclockwise as rotation directions of the cutting tool 8. The shaft portion 48 includes a plurality of (six in the shown form) segments arranged in an arc shape. The shaft portion 48 includes a clockwise shaft portion 48R forming the right half of the arc and a counterclockwise shaft portion 48L forming the left half of the arc. The clockwise head portion 49R is disposed at the lower end of the clockwise shaft portion 48R, and the counterclockwise head portion 49L is disposed at the lower end of the counterclockwise shaft portion 48L. The clockwise shaft portion 48R includes a first right segment 48Ra, a second right segment 48Rb, and a third right segment 48Rc. The counterclockwise shaft portion 48L includes a first left segment 48La, a second left segment 48Lb, and a third left segment 48Lc. The right segments 48Ra to 48Rc and the left segments 48La to 48Lc are arc-shaped portions having the same radius of curvature and the same central angle. For example, the central angle of each segment may be a value in the range of 40° to 50° or may be 45°. In addition, the invention is not limited to the configuration in which the respective segments have the same radius of curvature and the same central angle. For example, each segment may have a radius of curvature that forms a part of an ellipse.

As will be described later, the control unit 21 may control the display 22 according to the execution control mode in the root canal treatment device 10, so that all or some of the plurality of above-described segments of the shaft portion 48 and the clockwise head portion 49R and/or the counterclockwise head portion 49L are displayed on the display 22.

Figure 3B:
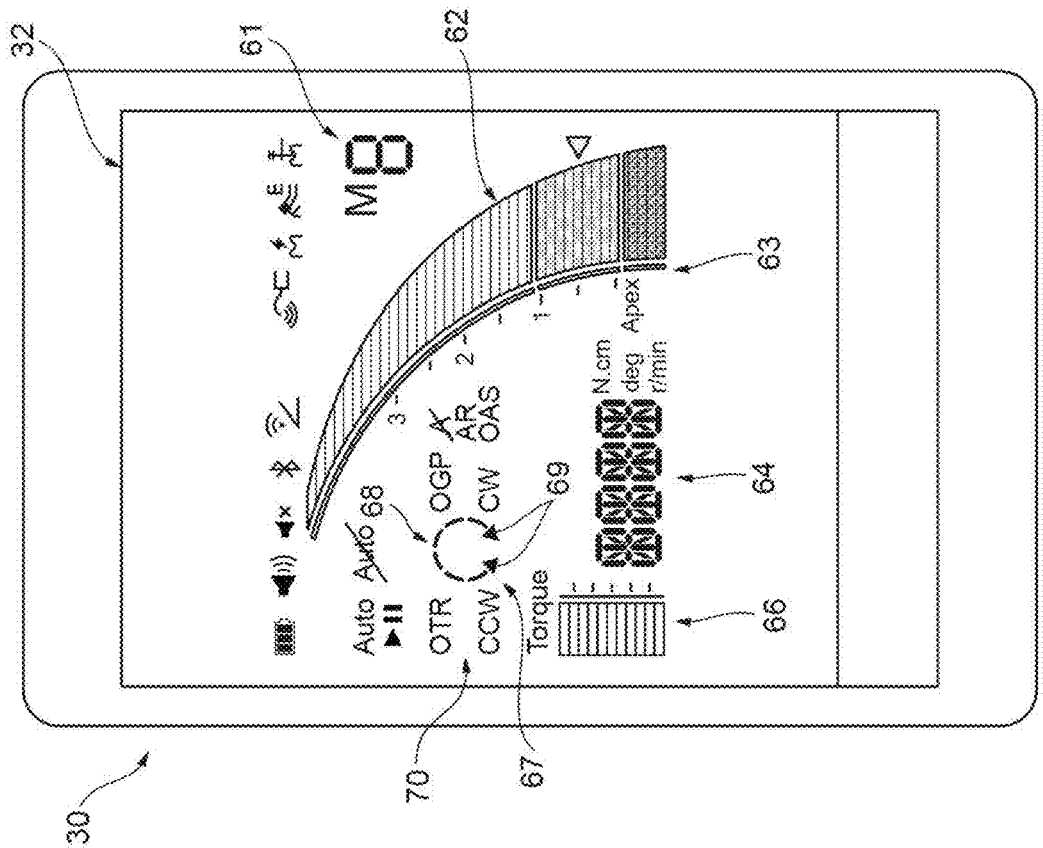
FIG. 3B is a diagram showing a tablet screen.
Figure 3A:
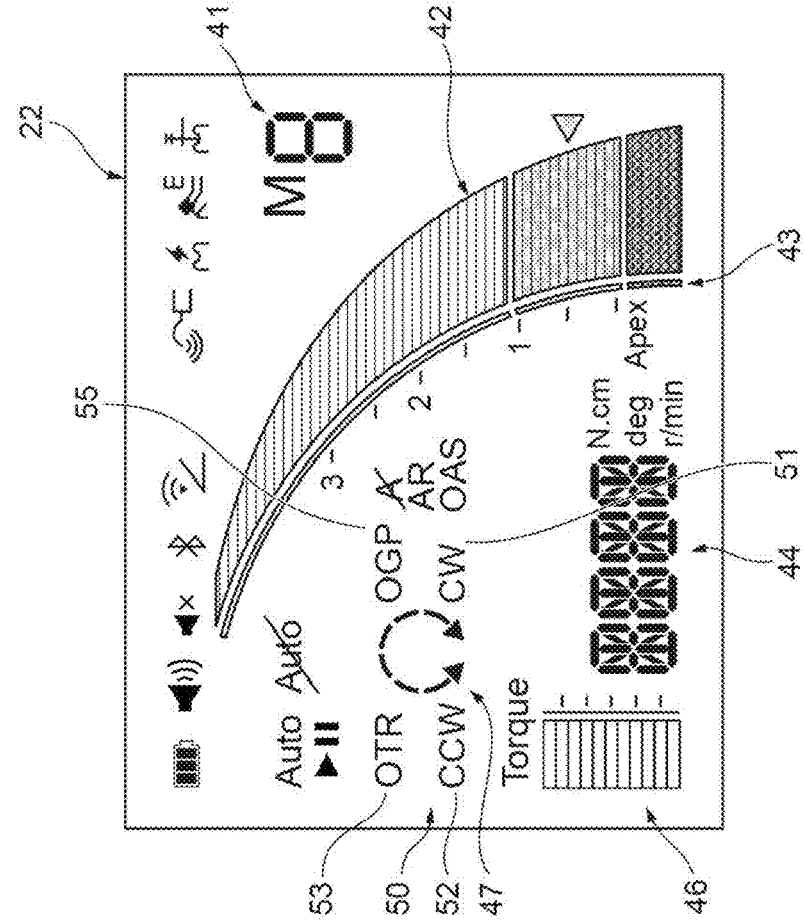
FIG. 3A is a diagram showing a display unit of a display apparatus.

On the other hand, as shown in FIG. 3B, the same display as on the display 22 is performed on the touch panel display 32 of the tablet 30 by the mirroring control. An operation mode display portion 61 for displaying a setting mode selected by the user, a dot display portion 62 including a large number of elements for displaying the measured root canal length in detail, a zone display portion 63 for displaying the root canal length in a stepwise manner by dividing the root canal length into a plurality of zones, a numerical display portion 64 for displaying the number of rotations of the cutting tool 8 and the like, and a dot display portion 66 including a large number of elements for displaying the value of torque applied to the cutting tool 8 are provided on the touch panel display 32. A control mode character notation 70 and a control mode FIG. 67 for indicating the execution control mode are provided on the touch panel display 32. The control mode FIG. 67 has a shaft portion 68 extending in an arc shape and a direction display portion 69 disposed at the lower right end (first end) and the lower left end (second end) of the shaft portion 68.

Figure 6:
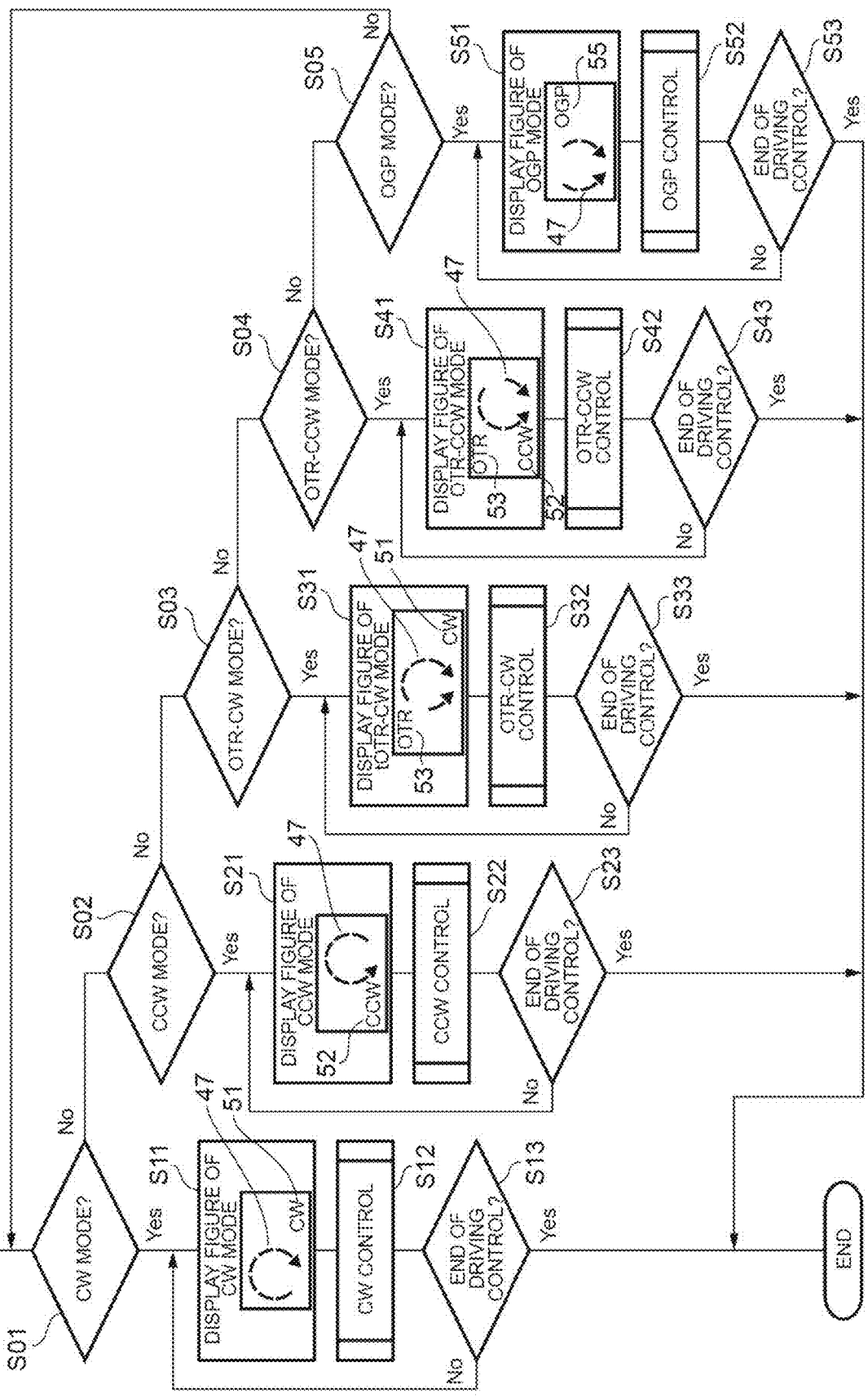
FIG. 6 is a flowchart showing a process performed by a control unit of a root canal treatment apparatus.
Figure 7A:
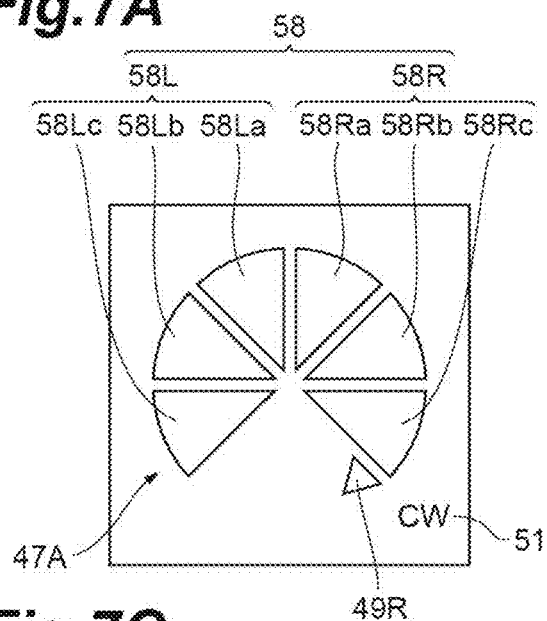
FIGS. 7A to 7E are diagrams showing display modes of first to fifth modes in a first modification example.
Figure 7B:
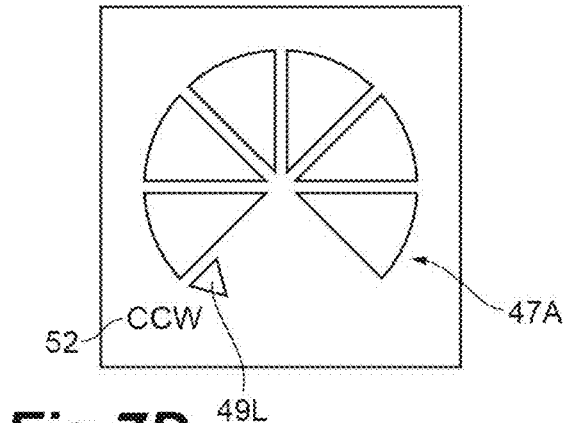
Figure 7C:
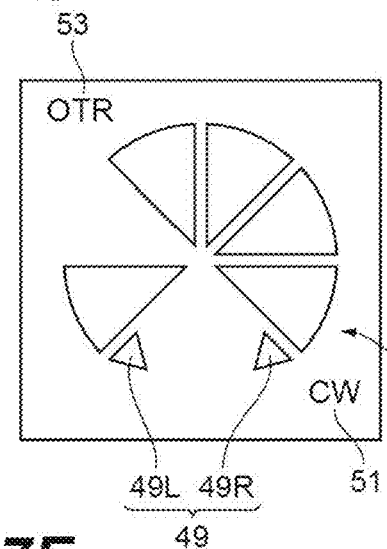
Figure 7D:
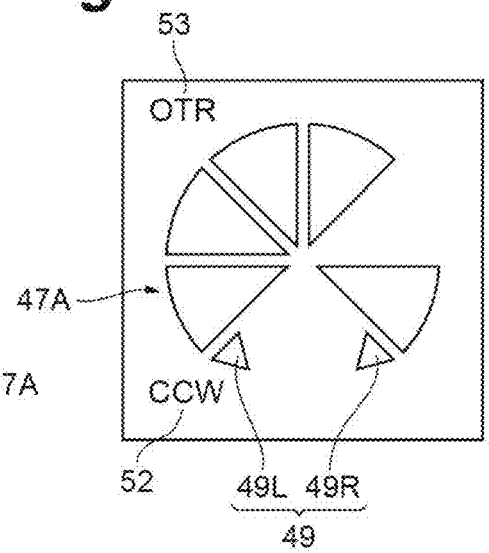
Figure 7E:
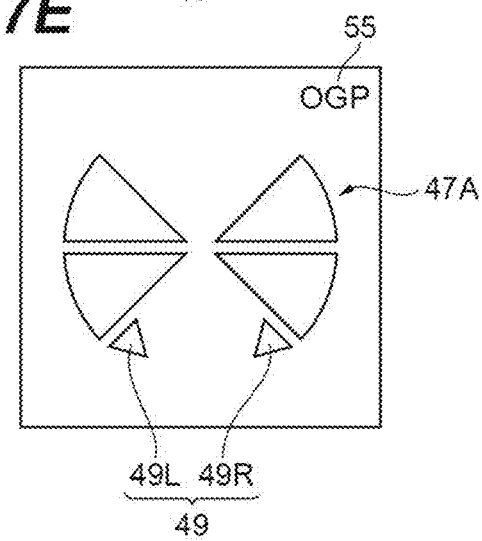
Figure 9A:
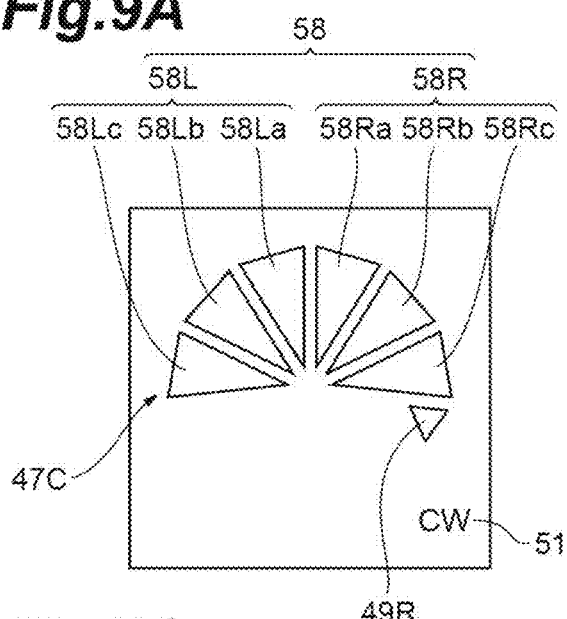
FIGS. 9A to 9E are diagrams showing display modes of first to fifth modes in a third modification example.
Figure 9B:
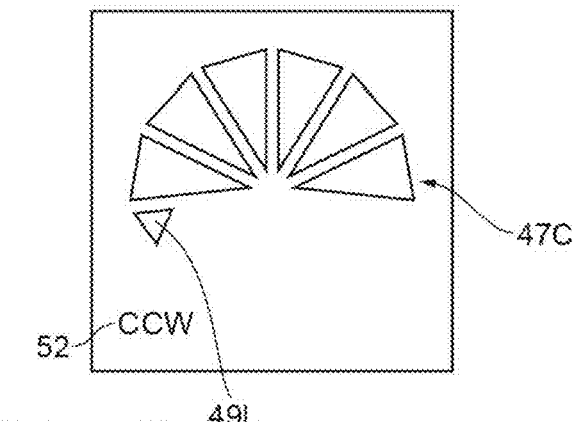
Figure 9C:
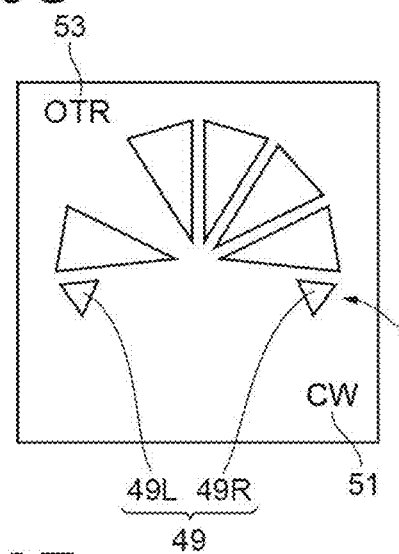
Figure 9D:
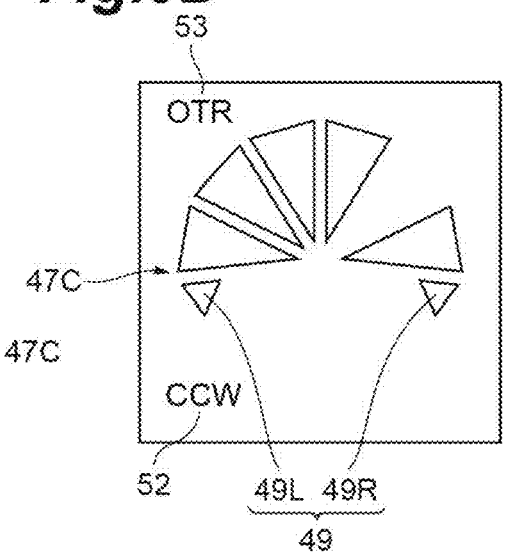
Figure 9E:
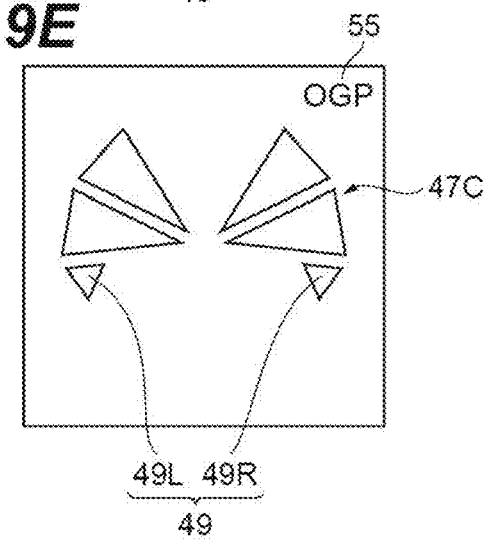

Next, a process (display control method in the root canal treatment device 10) performed by the control unit 11 and the control unit 21 will be described with reference to FIG. 6. FIG. 6 is a flowchart showing the process performed by the control unit 11 and the control unit 21. First, the control unit 21 determines whether or not the CW mode has been selected by the operation of the operation unit 23 or the touch panel display 32 (step S01). When it is determined that the CW mode has been selected (step S01; Yes), the control unit 21 may cause the display 22 to display a figure of the CW mode on (step S11). When the user steps on the foot controller 9, the control unit 11 controls the motor driver 12 and the micromotor 6a in the CW mode (step S12), so that the cutting tool 8 continues to rotate clockwise at a predetermined rotation speed (a predetermined number of rotations). When it is determined that the driving control based on the CW mode has ended (step S13; Yes), the control unit 11 ends the driving control for the motor driver 12 and the micromotor 6a. In addition, while the user is stepping on the foot controller 9, the cutting tool 8 continues to rotate according to the execution control mode. However, when the user releases the foot controller 9, the control by the control unit 11 and the control unit 21 ends, or the process return to step S01. When it is determined that the driving control based on the CW mode has not ended (step S13; No), the control unit 21 performs the process of step S11, and the control unit 11 performs the process of step S12. In step S01, when the control unit 21 determines that the CW mode has not been selected as a control mode (step S01; No), the control unit 21 performs the determination of step S02.

In the display control of the CW mode in step S11, the control mode FIG. 47 of the display 22 may include all the segments of the shaft portion 48 and only the clockwise head portion 49R. In the control mode FIG. 47, only the counterclockwise head portion 49L is not displayed. Accordingly, when the execution control mode is the CW mode, the control unit 21 may cause the display 22 to display the entire shaft portion 48 and only the clockwise head portion 49R. In addition, in the CW mode, the control unit 21 may control the display 22 not to display the entirety or a part of the counterclockwise shaft portion 48L in the shaft portion 48.

By the figure display described above, the user can intuitively understand that the cutting tool 8 is in the execution control mode in which the cutting tool 8 continues to rotate clockwise. In the example, the control mode character notation 50 is displayed together with the control mode FIG. 47. In the display control of the CW mode, the CW notation 51 is displayed together with the control mode FIG. 47 described above. Therefore, the user can more clearly understand that the CW mode is being executed.

The control unit 21 determines whether or not the CCW mode has been selected by the operation of the operation unit 23 or the touch panel display 32 (step S02). When it is determined that the CCW mode has been selected (step S02; Yes), the control unit 21 may cause the display 22 to display a figure of the CCW mode (step S21). When the user steps on the foot controller 9, the control unit 11 controls the motor driver 12 and the micromotor 6a in the CCW mode (step S22), so that the cutting tool 8 continues to rotate counterclockwise at a predetermined rotation speed (a predetermined number of rotations). When it is determined that the driving control based on the CCW mode has ended (step S23; Yes), the control unit 11 ends the driving control for the motor driver 12 and the micromotor 6a. When it is determined that the driving control based on the CCW mode has not ended (step S23; No), the control unit 21 performs the process of step S21, and the control unit 11 performs the process of step S22. In step S02, when the control unit 21 determines that the CCW mode has not been selected as a control mode (step S02; No), the control unit 21 performs the determination of step S03.

In the display control of the CCW mode in step S21, the control mode FIG. 47 of the display 22 includes all the segments of the shaft portion 48 and only the counterclockwise head portion 49L. In the control mode FIG. 47, only the clockwise head portion 49R is not displayed. Accordingly, when the execution control mode is the CCW mode, the control unit 21 may cause the display 22 to display the entire shaft portion 48 and only the counterclockwise head portion 49L. In addition, in the CCW mode, the control unit 21 may control the display 22 not to display the entirety or a part of the clockwise shaft portion 48R in the shaft portion 48. By the figure display described above, the user can intuitively understand that the cutting tool 8 is in the execution control mode in which the cutting tool 8 continues to rotate counterclockwise. In addition, in the display control of the CCW mode, the CCW notation 52 is displayed together with the control mode FIG. 47 described above. Therefore, the user can more clearly understand that the CCW mode is being executed.

The control unit 21 determines whether or not the OTR-CW mode has been selected by the operation of the operation unit 23 or the touch panel display 32 (step S03). When it is determined that the OTR-CW mode has been selected (step S03; Yes), the control unit 21 may cause the display 22 to display a figure of the OTR-CW mode (step S31). When the user steps on the foot controller 9, the control unit 11 controls the motor driver 12 and the micromotor 6a in the OTR-CW mode (step S32), so that the cutting tool 8 rotates counterclockwise when the torque value becomes equal to or greater than a predetermined threshold value while the cutting tool 8 is rotating clockwise. In the process of step S32, the control unit 11 determines whether the torque value is equal to or greater than the predetermined threshold value or less than the predetermined threshold value. When it is determined that the driving control based on the OTR-CW mode has ended (step S33; Yes), the control unit 11 ends the driving control for the motor driver 12 and the micromotor 6a. When it is determined that the driving control based on the OTR-CW mode has not ended (step S33; No), the control unit 21 performs the process of step S31, and the control unit 11 performs the process of step S32. In step S03, when the control unit 21 determines that the OTR-CW mode has not been selected as a control mode (step S03; No), the control unit 21 performs the determination of step S04.

In the display control of the OTR-CW mode in step S31, the control mode FIG. 47 of the display 22 includes all the segments of the clockwise shaft portion 48R, some of the segments of the counterclockwise shaft portion 48L, and both the clockwise head portion 49R and the counterclockwise head portion 49L. In the control mode FIG. 47, only the second left segment 48Lb of the counterclockwise shaft portion 48L is not displayed. Accordingly, when the execution control mode is the OTR-CW mode, the control unit 21 may cause the display 22 to display both the clockwise head portion 49R and the counterclockwise head portion 49L, and may cause the display 22 not to display only a portion close to the lower left end (second end) of the shaft portion 48. The OTR-CW mode is one of "predetermined execution control modes" described in the claims. In addition, in this display example, the "portion close to the lower left end of the shaft portion 48" is the second left segment 48Lb, but the "portion close to the lower left end of the shaft portion 48" may be the first left segment 48La or the third left segment 48Lc. By the figure display described above, the user can intuitively understand that the cutting tool 8 is in the execution control mode in which the cutting tool 8 rotates clockwise but rotates counterclockwise when the torque value becomes equal to or greater than a predetermined threshold value. In addition, in the display control of the OTR-CW mode, the OTR notation 53 and the CW notation 51 are displayed together with the control mode FIG. 47 described above. Therefore, the user can more clearly understand that the OTR-CW mode is being executed.

The control unit 21 determines whether or not the OTR-CCW mode has been selected by the operation of the operation unit 23 or the touch panel display 32 (step S04). When it is determined that the OTR-CCW mode has been selected (step S04; Yes), the control unit 21 may cause the display 22 to display a figure of the OTR-CCW mode (step S41). When the user steps on the foot controller 9, the control unit 11 controls the motor driver 12 and the micromotor 6a in the OTR-CCW mode (step S42), so that the cutting tool 8 rotates clockwise when the torque value becomes equal to or greater than a predetermined threshold value while the cutting tool 8 is rotating counterclockwise. In the process of step S42, the control unit 11 determines whether the torque value is equal to or greater than the predetermined threshold value or less than the predetermined threshold value. When it is determined that the driving control based on the OTR-CCW mode has ended (step S43; Yes), the control unit 11 ends the driving control for the motor driver 12 and the micromotor 6a. When it is determined that the driving control based on the OTR-CCW mode has not ended (step S43; No), the control unit 21 performs the process of step S41, and the control unit 11 performs the process of step S42. In step S04, when the control unit 21 determines that the OTR-CCW mode has not been selected as a control mode (step S04; No), the control unit 21 performs the determination of step S05.

In the display control of the OTR-CCW mode in step S41, the control mode FIG. 47 of the display 22 includes all the segments of the counterclockwise shaft portion 48L, some of the segments of the clockwise shaft portion 48R, and both the clockwise head portion 49R and the counterclockwise head portion 49L. In the control mode FIG. 47, only the second right segment 48Rb of the clockwise shaft portion 48R is not displayed. Accordingly, when the execution control mode is the OTR-CCW mode, the control unit 21 may cause the display 22 to display both the clockwise head portion 49R and the counterclockwise head portion 49L, and may cause the display 22 not to display only a portion close to the right left end (first end) of the shaft portion 48. The OTR-CCW mode is one of "predetermined execution control modes" described in the claims. In addition, in this display example, the "portion close to lower right end of the shaft portion 48" is the second right segment 48Rb, but the "portion close to the lower right end of the shaft portion 48" is the first right segment 48Ra or the third right segment 48Rc. By the figure display described above, the user can intuitively understand that the cutting tool 8 is in the execution control mode in which the cutting tool 8 rotates counterclockwise but rotates clockwise when the torque value becomes equal to or greater than a predetermined threshold value. In addition, in the display control of the OTR-CCW mode, the OTR notation 53 and the CCW notation 52 are displayed together with the control mode FIG. 47 described above. Therefore, the user can more clearly understand that the OTR-CCW mode is being executed.

The control unit 21 determines whether or not the OGP mode has been selected by the operation of the operation unit 23 or the touch panel display 32 (step S05). When it is determined that the OGP mode has been selected (step S05; Yes), the control unit 21 may cause the display 22 to display a figure of the OGP mode (step S51). When the user steps on the foot controller 9, the control unit 11 controls the motor driver 12 and the micromotor 6a in the OGP mode (step S52), so that the cutting tool 8 rotates at a predetermined rotation speed so as to repeat clockwise and counterclockwise rotation. When it is determined that the driving control based on the OGP mode has ended (step S53; Yes), the control unit 11 ends the driving control for the motor driver 12 and the micromotor 6a. When it is determined that the driving control based on the OGP mode has not ended (step S53; No), the control unit 21 performs the process of step S51, and the control unit 11 performs the process of step S52. In step S05, when the control unit 21 determines that the OGP mode has not been selected as a control mode (step S05; No), the control unit 21 performs the determination of step S01.

In the display control of the OGP mode in step S51, the control mode FIG. 47 of the display 22 includes some of the segments of the clockwise shaft portion 48R, all the segments of the counterclockwise shaft portion 48L, and both the clockwise head portion 49R and the counterclockwise head portion 49L. In the control mode FIG. 47, only the first right segment 48Ra and the first left segment 48La are not displayed. Accordingly, when the execution control mode is the OGP mode, the control unit 21 may cause the display 22 to display both the clockwise head portion 49R and the counterclockwise head portion 49L, and may cause the display 22 not to display only a middle portion between the lower right end and the lower left end of the shaft portion 48. The OGP mode is one of "predetermined execution control modes" described in the claims. In addition, in the OGP mode, the control unit 21 may control the display 22 not to display the first right segment 48Ra, the second right segment 48Rb, the first left segment 48La, and the second left segment 48Lb. By the figure display described above, the user can intuitively understand that the cutting tool 8 is in the execution control mode in which the cutting tool 8 rotates so as to repeat clockwise and counterclockwise rotation. In addition, in the display control of the OGP mode, the OGP notation 55 is displayed together with the control mode FIG. 47 described above. Therefore, the user can more clearly understand that the OGP mode is being executed.

Through the series of processes described above, root canal enlargement treatment using the root canal treatment device 10 and display on the display 22 of the root canal length measuring device 20 are performed. In addition, in the example described above, each segment and each head portion are in a display mode in which these continue to light. However, based on the display shown in FIG. 6, the shaft portion 48 and a predetermined portion of the direction display portion 49 may blink. The same applies to various modification examples described later.

In the example root canal length measuring device 20, an execution control mode that is actually executed is shown as a figure on the display 22. In order to display this figure, a plurality of elements are provided on the display 22. By the control unit 21, the entirety or a part of the shaft portion 48 extending in an arc shape and the clockwise head portion 49R and/or the counterclockwise head portion 49L disposed at the lower right end and the lower left end thereof are displayed on the display 22. As a display form (display method) of the shaft portion 48 and the direction display portion 49, instead of simply turning on and off the shaft portion 48 and the direction display portion 49, various forms can be adopted in which a part of the shaft portion 48 is displayed or either or both of the clockwise head portion 49R and the counterclockwise head portion 49L of the direction display portion 49 are displayed. Therefore, it is possible to display a figure that matches the rotation mode of the cutting tool 8, or the control mode, and it becomes easy for the user to grasp at a glance the execution control mode executed in the root canal treatment device 10. Conventionally, it has been difficult to easily grasp the control mode based on the display on the display unit. However, in the example, since the user can grasp the control mode from the figure by viewing the display unit, it is possible to grasp the control mode easily and instantly. These effects are similarly obtained for the user who sees the touch panel display 32 of the tablet 30 or a person other than the user.

In the case of a predetermined execution control mode, a part of the shaft portion 48 and both the head portions are displayed on the display unit. Since only a part of the shaft portion is displayed and both the head portions are displayed together with this, it is possible to express not only a simple rotation in the first or second direction but also a complicated movement of the cutting tool.

In particular, in the OTR-CW mode and the OTR-CCW mode, unlike in the CW mode and the CCW mode, the cutting tool 8 makes complicated movements. In either the OTR-CW mode or the OTR-CCW mode, a part of the shaft portion 48 and both the head portions are displayed, so that the complicated movement of the cutting tool 8 can be expressed.

By appropriately combining the displays of the shaft portion 48 and the direction display portion 49, it is possible to express information indicating whether the rotation direction is clockwise or counterclockwise, information indicating whether the main rotation direction is clockwise or counterclockwise, and the like. The user can easily grasp which control mode among the plurality of control modes is being executed.

In the CW mode or the CCW mode, the user can easily grasp whether the cutting tool 8 is rotating clockwise or counterclockwise by switching the head portion to be displayed under the control of the control unit 21.

In the OTR-CW mode or the OTR-CCW mode, the user can easily grasp that the cutting tool 8 is rotating both clockwise and counterclockwise. In addition, since one of the lower right end side and the lower left end side of the shaft portion 48 is longer than the other, the user can easily grasp which is the main rotation direction. By appropriately combining the displays of the shaft portion 48 and the direction display portion 49, it is possible to express that clockwise rotation and counterclockwise rotation are repeated. The user can easily grasp which control mode among the plurality of control modes is being executed.

In the OGP mode, since the left and right portions (the lower left side and the lower right side) of the shaft portion 48 have the same length, the user can easily grasp whether the cutting tool is repeatedly rotating clockwise and counterclockwise.

The shaft portion 48 includes four or more (six in the example) segments arranged in an arc shape. By turning on, turning off, or blinking each segment of the shaft portion 48, the user can more easily grasp the control mode. Since the display control of a figure is also simplified, it is easy to control the display of a figure.

It is to be understood that not all aspects, advantages and features described herein may necessarily be achieved by, or included in, any one particular example. Indeed, having described and illustrated various examples herein, it should be apparent that other examples may be modified in arrangement and detail.

For example, as shown in FIGS. 7A to 7E, a control mode FIG. 47A having a band portion 58 extending in a fan shape and a triangular direction display portion 49 may be used. In the control mode FIG. 47A, six segments are arranged in a fan shape. The band portion 58 includes a plurality of (six in the shown form) segments arranged in a fan shape. The band portion 58 includes a clockwise band portion 58R forming the right half of the arc and a counterclockwise band portion 58L forming the left half of the arc. The clockwise head portion 49R is disposed at the lower end of the clockwise band portion 58R, and the counterclockwise head portion 49L is disposed at the lower end of the counterclockwise band portion 58L. The clockwise band portion 58R includes a first right segment 58Ra, a second right segment 58Rb, and a third right segment 58Rc. The counterclockwise band portion 58L includes a first left segment 58La, a second left segment 58Lb, and a third left segment 58Lc. The positions and the range of the segments in the band portion 58 may be similar to the positions and the range of the segments in the shaft portion 48.

In addition, as shown in FIGS. 8A to 8E, a control mode FIG. 47B having a band portion 58 extending in a fan shape and a triangular direction display portion 49 may be used. In the control mode FIG. 47B, six segments are arranged in a fan shape, but a central space C is provided in a central portion of the control mode FIG. 47B. In the display form, the central portion is cut out. In addition, as shown in FIGS. 9A to 9E, a control mode FIG. 47C having a band portion 58 extending in a fan shape and a triangular direction display portion 49 may be used. In the control mode FIG. 47C, an angle range in which six fan-shaped segments are provided is smaller than that in the control mode FIGS. 47, 47A, and 47B described above.

In addition, as shown in FIGS. 10A to 10E, a control mode FIG. 47D having a shaft portion 48 extending in an arc shape and a triangular direction display portion 49 may be used. In the control mode FIG. 47D, a plurality of segments are not used, a dot matrix or the like is used, and a continuous shaft portion 48 is provided. In this case, in the OTR-CW mode, the control mode FIG. 47D includes a left non-display portion 45L, which is a portion where the arc is cut out, on the left side of the shaft portion 48. In the OTR-CCW mode, the control mode FIG. 47D includes a left non-display portion 45L, which is a portion where the arc is cut out, on the right side of the shaft portion 48. In the OGP mode, the control mode FIG. 47D includes a central non-display portion 45M, which is a portion where the arc is cut out, at the upper center of the shaft portion 48. In addition, there may be no gap between the shaft portion 48 and the left and right head portions 49R and 49L, and these may be continuous.

One or more of the five types of control modes described above may be omitted. For example, a plurality of modes may include three or four types of control modes obtained by adding one or two of the OTR-CW mode, the OTR-CCW mode, and the OGP mode to the CW mode and the CCW mode. Alternatively, either the CW mode or the CCW mode may be omitted. The plurality of control modes may include six or more types of control modes obtained by combining any of clockwise, counterclockwise, and stop. Regardless of which control modes are included, the user can grasp at a glance the execution control mode executed in the root canal treatment device 10 by displaying the entirety or a part of the shaft portion or the band portion and the first head portion and/or the second head portion on the display.

In the root canal treatment device 10, not only the control by the foot controller 9 but also the operation of reversing the rotation direction or the operation of stopping the reversal of the rotation direction may be performed according to the user's setting. For example, the root canal treatment device 10 may have a function called apical reverse. With the apical reverse function, when the distal end position of the file reaches a preset position in the root canal, the rotation direction is automatically reversed. Even in such a case, the user can grasp at a glance the execution control mode executed in the root canal treatment device 10 by displaying the entirety or a part of the shaft portion or the band portion and the first head portion and/or the second head portion on the display.

The number of segments forming the shaft portion or the band portion may be an even number or an odd number. The number of segments may be four, five, or seven or more. The central angles (or perimeters) of respective segments arranged in an arc shape or a fan shape may be different.

The control mode character notation 50 may not be adjacent to the control mode FIG. 47 and may be displayed at a position away from the control mode FIG. 47. The control mode character notation 50 may be omitted.

What is claimed is:

1. A display apparatus for displaying a control mode of a cutting tool attached to a root canal treatment device, comprising:
   a display configured to display a figure indicating an execution control mode selected from among a plurality of control modes of the cutting tool; and
   a controller configured to control the display to display the figure,
   wherein a plurality of elements for displaying the figure include:
   a shaft portion extending in an arc shape or a band portion extending in a fan shape;
   a first head portion disposed at a first end of the shaft portion or the band portion to indicate a first direction of rotation of the cutting tool; and a second head portion disposed at a second end of the shaft portion or the band portion to indicate a second direction of rotation of the cutting tool, wherein the controller is further configured to control the display to display at least part of one or more of the plurality of elements according to the selected execution control mode of the cutting tool, wherein the plurality of control modes includes a predetermined mode in which the cutting tool is sequentially rotated in the first direction for a first period of time and in the second direction for a second period of time, wherein the first period of time is longer than the second period of time, so as to reverse the rotation of the cutting tool based, at least in part, on a determination that a torque threshold is reached during the rotation of the cutting tool in the first direction, wherein in response to the controller determining that the selected execution control mode corresponds to the predetermined mode, the display is caused to display both the first head portion and the second head portion together with a part of the shaft portion or the band portion, so that the shaft portion or the band portion is split into a first end portion that is adjacent to the first head portion and a second end portion that is adjacent to the second head portion, and wherein the first end portion, representing the first period of time that the cutting tool is rotated in the first direction, is longer than the second end portion, representing the second period of time that the cutting tool is rotated in the second direction.

2. The display apparatus according to claim 1, wherein the plurality of control modes include a first mode in which the cutting tool is configured to exclusively rotate in the first direction of rotation, a second mode in which the cutting tool is configured to exclusively rotate in the second direction of rotation, a third mode that corresponds to the predetermined mode, and a fourth mode in which the cutting tool is rotated in the second direction of rotation for a longer period of time than in the first direction of rotation, and wherein in response to the controller determining that the selected execution control mode corresponds to the fourth mode, the display is caused to display both the first head portion and the second head portion together with a part of the shaft portion or the band portion in which the second end portion is longer than the first end portion.

3. The display apparatus according to claim 2, wherein, when the execution control mode is the first mode, the controller causes the display to display at least part of the shaft portion or the band portion together with the first head portion, without displaying the second head portion, and when the execution control mode is the second mode, the controller causes the display to display at least part of the shaft portion or the band portion together with the second head portion, without displaying the first head portion.

4. The display apparatus according to claim 2, wherein the shaft portion or the band portion includes a plurality of segments, wherein, when the execution control mode is the third mode, the controller causes the display to display both the first head portion and the second head portion without displaying at least one segment among the plurality of segments of the shaft portion or the band portion, that is located closer to the second head portion than to the first head portion, and wherein when the execution control mode is the fourth mode, the controller causes the display to display both the first head portion and the second head portion without displaying at least one segment among the plurality of segments of the shaft portion or the band portion, that is located closer to the first head portion than to the second head portion.

5. The display apparatus according to claim 1, wherein the plurality of control modes include an additional mode in which the cutting tool reciprocates between the first direction of rotation and the second direction of rotation, and wherein in response to the controller determining that the selected execution control mode corresponds to the additional mode, the display is caused to display both the first head portion and the second head portion together with a part of the shaft portion or the band portion, in which the second end portion is equal in length to the first end portion, and without displaying a middle portion of the shaft portion or the band portion, located between the first end portion and the second end portion.

6. The display apparatus according to claim 1, wherein the shaft portion or the band portion includes at least four or more segments arranged in the arc shape or the fan shape.

7. The display apparatus according to claim 1, wherein the controller is configured to control the display to:
display a first character notation located adjacent to the first head portion of the figure to indicate that the first direction of rotation is a clockwise direction;
display a second character notation adjacent to the second head portion to indicate that the second direction of rotation is a counterclockwise direction; and
display at least one additional character notation adjacent to the figure, in response to determining that the selected execution control mode corresponds to the predetermined mode.

8. A display apparatus comprising:
a display configured to display a figure indicating a user selected execution control mode executed in a cutting tool of a root canal treatment device; and
a controller configured to control the display to display the figure according to the selected execution control mode, wherein a plurality of elements for displaying the figure include:
an arc shaped portion including a plurality of segments;
a first head portion disposed at a first end of the arc shaped portion to indicate a first direction of rotation of the cutting tool; and
a second head portion disposed at a second end of the arc shaped portion to indicate a second direction of rotation of the cutting tool, wherein the selected execution control mode is selected from among a plurality of control modes that includes a mode in which the cutting tool is sequentially rotated in the first direction and in the second direction, and wherein in response to the controller determining that the selected execution control mode is the mode in which the cutting tool is sequentially rotated in the first direction and in the second direction, the display is caused to display both the first head portion and the second head portion together with a part of the arc shaped portion so that at least one segment among the plurality of segments of the arc shaped portion is not displayed.

9. The display apparatus according to claim 8,
wherein in the mode in which the cutting tool is sequentially rotated in the first direction and in the second direction, the part of the arc shaped portion that is displayed is split by the at least one segment that is not displayed, into a first end portion and a second end portion,
wherein the first end portion includes a first number of the plurality of segments, that is located adjacent to the first head portion, and
wherein the second end portion includes a second number of the plurality of segments, that is located adjacent to the second head portion.

10. The display apparatus according to claim 9,
wherein, the mode in which the cutting tool is sequentially rotated in the first direction and in the second direction is a predetermined mode in which the cutting tool is set to repeatedly alternate between the first direction of rotation and the second direction of rotation, and
wherein in the predetermined mode, the at least one segment that is not displayed corresponds to a middle portion of the arc shaped portion located between the first number of the plurality of segments and the second number of the plurality of segments.

11. The display apparatus according to claim 8, wherein the mode in which the cutting tool is sequentially rotated in the first direction and in the second direction is selected from: a first predetermined mode in which the cutting tool is rotated in the first direction of rotation for a longer period of time than in the second direction of rotation; and a second predetermined mode in which the cutting tool is rotated in the second direction of rotation for a longer period of time than in the first direction of rotation, so as to reverse the rotation of the cutting tool based, at least in part, on a determination that a torque threshold is reached during the rotation of the cutting tool,
wherein the at least one segment of the arc shaped portion that is not displayed is located closer to the second head portion than to the first head portion, in response to the controller determining that the selected execution control mode is the first predetermined mode, and
wherein the at least one segment of the arc shaped portion that is not displayed is located closer to the first head portion than to the second head portion, in response to the controller determining that the selected execution control mode is the second predetermined mode.

12. The display apparatus according to claim 10,
wherein, in response to determining that the selected execution control mode corresponds to the first predetermined mode, the part of the arc shaped portion that is displayed is split so that a first number of the plurality of segments of the arc shaped portion that is displayed adjacent to the first head portion is greater than a second number of the plurality of segments of the arc shaped portion that is displayed adjacent to the second head portion, and
wherein, in response to determining that the selected execution control mode corresponds to the second predetermined mode, the part of the arc shaped portion that is displayed is split so that the second number of the plurality of segments displayed adjacent to the second head portion is greater than the first number of the plurality of segments displayed adjacent to the second head portion.

13. The display apparatus according to claim 8, wherein the plurality of segments of the arc shaped portion are arranged to form an arc-shape or a fan shape.

14. The display apparatus according to claim 8, wherein the controller is configured to control the display to:
display a first character notation to indicate the first direction of rotation;
display a second character notation to indicate the second direction of rotation; and
display at least one additional character notation in response to determining that the selected execution control mode corresponds to the mode in which the cutting tool is sequentially rotated in the first direction and in the second direction.

15. A display apparatus comprising:
a display configured to display a figure indicating a user selected execution control mode executed in a cutting tool of a root canal treatment device; and
a controller configured to control the display to display the figure according to the selected execution control mode,
wherein a plurality of elements for displaying the figure include:
an arc shaped portion;
a first head portion disposed adjacent a first end of the arc shaped portion to indicate a first direction of rotation of the cutting tool; and
a second head portion disposed adjacent a second end of the arc shaped portion to indicate a second direction of rotation of the cutting tool,
wherein the selected execution control mode is selected among a plurality of control modes including a first mode in which the cutting tool is set to exclusively rotate in the first direction, a second mode in which the cutting tool is set to exclusively rotate in the second direction, and an additional mode in which the cutting tool is set to sequentially rotate in the first direction and in the second direction, and
wherein the controller is configured to control the display to:
display a first character notation to indicate that the selected execution control mode corresponds to the first mode;
display a second character notation to indicate that the selected execution control mode corresponds to the second mode; and
display both the first head portion and the second head portion together with at least one additional character notation, to indicate that the selected execution control mode corresponds to the additional mode in which the cutting tool is sequentially rotated in the first direction and in the second direction.

16. The display apparatus according to claim 15, wherein the display is configured to:
display at least part of the arc shaped portion and the first head portion, without displaying the second head portion, in response to the controller determining that the selected execution control mode corresponds to the first mode; and
display at least part of the arc shaped portion together with the second head portion, without displaying the first head portion, in response to the controller determining that the selected execution control mode corresponds to the second mode.

17. The display apparatus according to claim 15,
wherein the additional mode is a third mode in which the cutting tool is rotated in the first direction of rotation for a longer period of time than in the second direction of rotation, and
wherein the display is configured to display both the first head portion and the second head portion without displaying the second end of the arc shaped portion adjacent the second head portion, in response to the controller determining that the selected execution control mode corresponds to the third mode.

18. The display apparatus according to claim 15,
wherein the additional mode is selected from:
   a third mode in which the cutting tool is rotated in the first direction of rotation for a longer period of time than in the second direction of rotation; and
   a fourth mode in which the cutting tool is rotated in the second direction of rotation for a longer period of time than in the first direction of rotation,
wherein the display is configured to display both the first head portion and the second head portion without displaying the second end of the arc shaped portion adjacent the second head portion, in response to the controller determining that the selected execution control mode corresponds to the third mode, and
wherein the display is configured to display both the first head portion and the second head portion without displaying the first end of the arc shaped portion adjacent the first head portion, in response to the controller determining that the selected execution control mode corresponds to the fourth mode.

19. The display apparatus according to claim 15,
wherein the additional mode is a third mode in which the cutting tool is rotated in the first direction of rotation for a longer period of time than in the second direction of rotation, and
wherein in response to the controller determining that the selected execution control mode corresponds to the third mode, the display is caused to additionally display a part of the arc shaped portion, so that the arc shaped portion is split into a first end portion that is adjacent to the first head portion and a second end portion that is adjacent to the second head portion, wherein the first end portion is longer than the second end portion.

20. The display apparatus according to claim 15,
wherein the additional mode is a predetermined mode in which a rotation direction of the cutting tool is reversed based, at least in part, on the controller determining that a torque threshold is reached during the rotation of the cutting tool in the first direction or the second direction,
wherein the first character notation includes a first string of letters to indicate that the first direction is a clockwise direction,
wherein the second character notation includes a second string of letters to indicate that the second direction is a counterclockwise direction, and
wherein the additional character notation includes an additional string of letters to indicate the predetermined mode.

* * * * *